(12) United States Patent
Wood

(10) Patent No.: US 11,904,106 B2
(45) Date of Patent: Feb. 20, 2024

(54) OBSTETRICAL URINARY CATHETER

(71) Applicant: Gregory Douglas Wood, Little Rock, AR (US)

(72) Inventor: Gregory Douglas Wood, Little Rock, AR (US)

( * ) Notice: Subject to any disclaimer, the term of this patent is extended or adjusted under 35 U.S.C. 154(b) by 359 days.

(21) Appl. No.: 17/153,061

(22) Filed: Jan. 20, 2021

(65) Prior Publication Data
US 2022/0226606 A1 Jul. 21, 2022

(51) Int. Cl.
*A61M 25/00* (2006.01)
*A61M 25/10* (2013.01)

(52) U.S. Cl.
CPC .. *A61M 25/0017* (2013.01); *A61M 25/10186* (2013.11); *A61M 2025/1081* (2013.01)

(58) Field of Classification Search
CPC ........ A61M 25/0017; A61M 25/10186; A61M 2025/1081; A61M 25/1011; A61M 2202/0494; A61B 17/42; A61B 17/4208; A61B 2017/4216; A61B 2017/4225; A61B 2017/4233; A61B 17/4241; A61B 5/0011

See application file for complete search history.

(56) References Cited

U.S. PATENT DOCUMENTS 2,849,002 A * 8/1958 Oddo ................. A61M 25/1011
606/192
3,154,077 A * 10/1964 Cannon .............. A61M 25/1011
606/192
3,509,884 A * 5/1970 William ............. A61M 25/1011
604/101.05
3,848,602 A * 11/1974 Gutnick ................. A61B 17/42
604/104
4,664,114 A * 5/1987 Ghodsian .............. A61M 29/02
604/104

(Continued)

FOREIGN PATENT DOCUMENTS

RU 2363503 C2 * 8/2009
RU 205903 U1 * 8/2021 ............. A61B 17/12

*Primary Examiner* — Adam Marcetich
(74) *Attorney, Agent, or Firm* — Lambert Shortell & Connaughton; David J. Connaughton, Jr.; Justin P. Tinger

(57) ABSTRACT

The invention provides an improved indwelling urinary catheter of the inflatable type having a unique, low profile device by which to retain the catheter within the bladder, so that urine can be removed therefrom while avoiding obstruction to the descending fetal vertex during the process of labor and delivery. Thus, making it better suited for obstetrical applications. The retaining device consumes less obstructing volume in the bladder than that which would ordinarily be consumed by a conventional Foley-style balloon, whereby both the frequency and severity of fetal vertex obstruction and its resulting increased time of labor, operative delivery and injury to maternal urologic tissue can be reduced. The obstetrical foley retains the tradition Foley-style balloon distal to the improved low-profile laboring balloon for insufflation in the event a surgical delivery by cesarean section is indicated. The traditional balloon with its larger volume allows easy identification of the bladder during surgical delivery. This unique design allows the added advantage of multiple options and uses in a single foley catheter without the need of changing catheters.

1 Claim, 1 Drawing Sheet

(56) References Cited

U.S. PATENT DOCUMENTS

| | | | | |
|---|---|---|---|---|
| 4,686,985 A * | 8/1987 | Lottick | A61M 29/02 | 606/192 |
| 4,693,704 A * | 9/1987 | Ogita | A61M 25/1011 | 604/100.01 |
| 5,209,754 A * | 5/1993 | Ahluwalia | A61B 17/4241 | 606/1 |
| 5,372,584 A * | 12/1994 | Zink | A61B 10/0291 | 604/97.02 |
| 5,417,657 A * | 5/1995 | Hauer | A61M 25/0017 | 604/523 |
| 5,624,399 A * | 4/1997 | Ackerman | A61B 17/42 | 606/119 |
| 6,102,929 A * | 8/2000 | Conway | A61M 25/10186 | 606/198 |
| 6,422,997 B1 * | 7/2002 | Green | A61M 25/0075 | 604/101.03 |
| 2006/0058831 A1 * | 3/2006 | Atad | A61M 25/1002 | 606/193 |
| 2007/0213661 A1 * | 9/2007 | Gobel | A61F 2/0013 | 604/96.01 |
| 2008/0215031 A1 * | 9/2008 | Belfort | A61B 17/12099 | 606/192 |
| 2009/0171268 A1 * | 7/2009 | Williams, Jr. | A61M 13/003 | 604/26 |
| 2011/0098683 A1 * | 4/2011 | Wiita | A61M 25/0069 | 604/544 |
| 2013/0096499 A1 * | 4/2013 | Tchirikov | A61B 17/0057 | 606/213 |
| 2015/0065807 A1 * | 3/2015 | Greenberg | A61B 1/05 | 600/207 |
| 2018/0055515 A1 * | 3/2018 | Greene, Jr. | A61B 17/1204 | |
| 2018/0264247 A1 * | 9/2018 | Mantri | A61B 17/0057 | |
| 2019/0008443 A1 * | 1/2019 | O'Dea | A61B 5/435 | |
| 2019/0091440 A1 * | 3/2019 | Lüning | A61M 25/10 | |
| 2020/0305742 A1 * | 10/2020 | Ghodsian | A61B 5/035 | |
| 2020/0383703 A1 * | 12/2020 | Atad | A61M 29/02 | |
| 2021/0196202 A1 * | 7/2021 | McKinney | A61M 25/1011 | |
| 2021/0322025 A1 * | 10/2021 | Greene | A61B 17/1204 | |
| 2022/0015805 A1 * | 1/2022 | Sabaris Vilas | A61M 27/00 | |

* cited by examiner

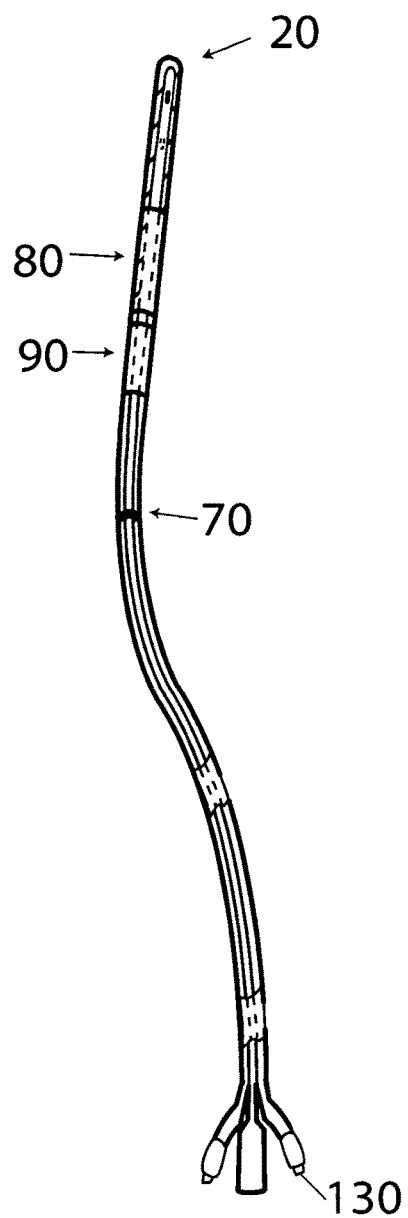
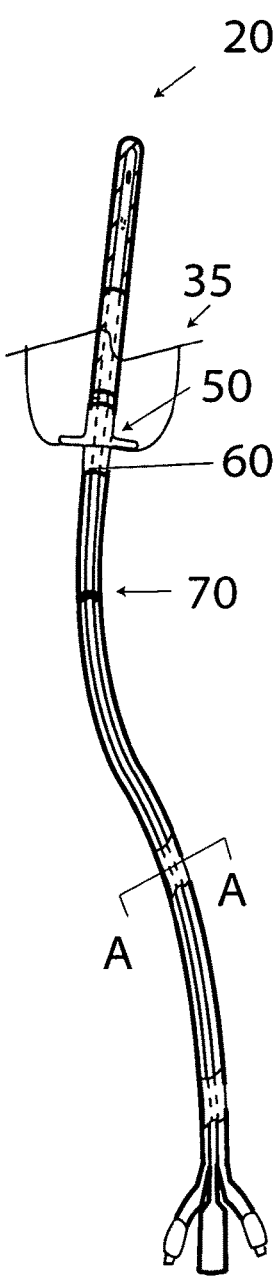
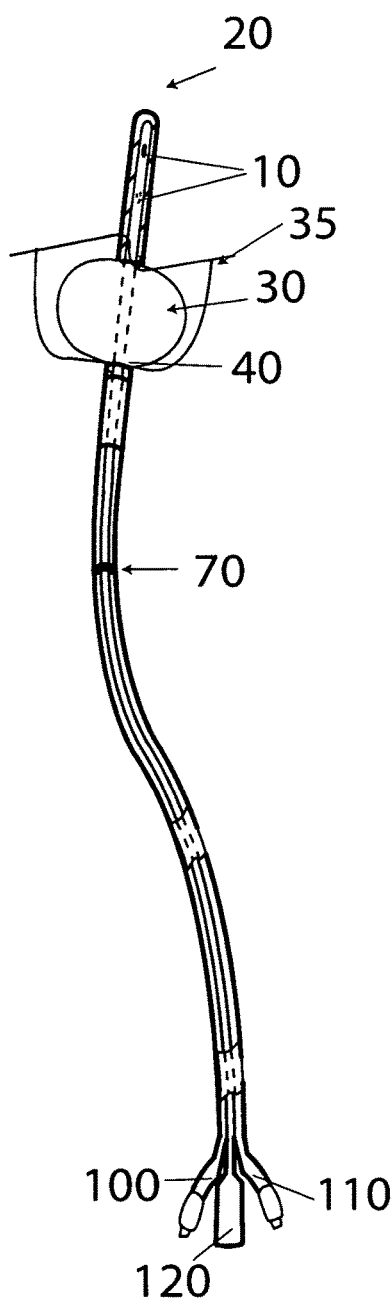
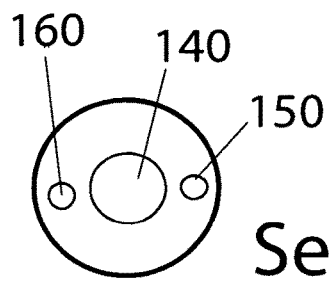
Fig. 1
Fig. 2
Fig. 3
Section A-A

OBSTETRICAL URINARY CATHETER

BACKGROUND OF THE INVENTION

1. Field of the Invention

This invention relates to an improved urinary catheter having a unique low profile by which to retain the catheter within the bladder so that urine can be removed therefrom during the labor and delivery process without obstruction of the fetal vertex and resulting iatrogenic obstruction of labor and injury to maternal urethral and bladder tissue.

2. Prior Art

Known to those skilled in the art, a conventional Foley catheter is inserted into the female urethral opening and through its length into the urinary bladder of a female patient until the proximal end of the catheter contacts the upper wall of the patient's bladder. The Foley catheter balloon is then inflated, while in situ, and the catheter is retracted slowly until the inflated balloon encounters some resistance against the lower bladder wall. The inflated balloon retains the catheter within the bladder so that urine can be removed therefrom and delivered to a bladder bag for disposal.

However, there are several significant problems which may arise as a consequence of using a conventional Foley catheter during the labor process. More particularly, an inflated Foley balloon typically assumes a spherical configuration which consumes a relatively large volume within the patient's bladder. The large volume consumed by the Foley balloon and in its current spherical configuration correspondingly increases the occurrence of direct obstruction of the descending fetal head and the arrest of the labor process and resulting increase in the rate of cesarean section. With prolonged obstruction the occurrence of injury to maternal urethra and bladder may occur resulting in loss of the physiological angle of the urethra, incontinence, and other chronic urinary complaints which may require surgical correction.

SUMMARY OF THE INVENTION

Briefly, an improved urinary catheter is disclosed by which to overcome the shortcomings of the Foley catheter. The catheter includes a low volume, low profile means by which to retain the catheter within the bladder so that urine may be removed therefrom without obstruction of the descending fetal vertex during the labor process. More particularly, the retaining means of the improved catheter has less obstruction volume and presence in the bladder than that which would ordinarily be consumed and obstructed by a conventional spherically shaped Foley balloon. Accordingly, both the frequency and severity of fetal vertex obstruction and maternal tissue injury by the application of excessive obstructive volume, such as that generated when a Foley balloon is inflated within the bladder, can be reduced. Thus, by eliminating the obstruction within the bladder, the patient will be less likely to incur an obstructed or arrested labor from iatrogenic cause and the subsequent increase in operative delivery and future urologic complications.

According to the embodiment of the invention, the retaining means is an additional inflatable balloon placed proximal to the traditional balloon having a thin, flat, flexible, pancake-like (rather than a spherical) configuration.

BRIEF DESCRIPTION OF THE DRAWINGS

FIG. 1 is a diagrammatic view of the obstetrical urinary bladder and urethral catheter in the deflated state.

FIG. 2 is a diagrammatic view of the obstetrical urinary bladder and urethral catheter with the labor balloon inflated and the standard balloon deflated.

FIG. 3 is a diagrammatic view of the obstetrical urinary bladder and urethral catheter with the standard balloon inflated and the labor balloon deflated.

Section A-A is a cross sectional view of the mid portion of the obstetrical urinary bladder and urethral catheter.

DESCRIPTION OF THE PREFERRED EMBODIMENT

The improved urinary catheter is now described while referring concurrently to FIGS. 1-3 of the drawings. In FIG. 1-3, the catheter is shown with the distal end, catheter tip 20 oriented at the top of the page. In FIG. 3, the obstetrical catheter includes a larger 10 cc conventional Foley-style retaining balloon 30 which is received within the patient's bladder 35. Balloon 30 is inflated, while in situ, so as to be seated against the relatively narrow neck of a bladder 35, whereby to prevent an inadvertent removal of the catheter therefrom. The balloon 30 is inflated with a 10 cc supply of fluid (e.g. water or isotonic or iso-osmotic fluid, or the like) via an inflation channel 150 (Section A-A) which extends longitudinally through catheter between the balloon 30 and a syringe docking port 130 having a check valve 110 associated therewith to prevent an inadvertent deflation of the balloon. As in a conventional catheter, the presently disclosed obstetrical catheter also includes a centrally disposed urine passage 140 (Section A-A) which extends longitudinally through the catheter from a urine inlet aperture 10 to the distal base 120 at which urine can be collected in a bladder bag (not shown) for disposal.

Unlike the conventional catheters, and as an important feature of the obstetrical catheter, a second inflatable balloon 50, FIG. 2 is incorporated into the catheter structure. In FIG. 2, the obstetrical catheter includes a smaller 3 cc flat unique low-profile retaining balloon 50 which is received within the patient's bladder 35. Balloon 50 is inflated, while in situ, so as to be seated against the relatively narrow neck of a bladder 35, whereby to prevent an inadvertent removal of the catheter therefrom. The balloon 50 is inflated with a 3 cc supply of fluid (e.g. water or isotonic or iso-osmotic fluid, or the like) via an inflation channel 160 (Section A-A) which extends longitudinally through catheter between the balloon 50 and a syringe docking port 130 having a check valve 100 associated therewith to prevent an inadvertent deflation of the balloon.

Referring now to FIG. 1 The obstetrical catheter has the deflated standard balloon sheath 80 and the deflated labor balloon sheath 90 on the distal end of the catheter just proximal to the urine inlet apertures. FIG. 1 shows the labor insertion marker 70 proximal to the labor balloon sheath 90. This labor insertion marker 70 is used to gauge the distance the obstetrical catheter should be inserted prior to inflating the labor balloon 50. When a obstetrical patient has a indication for a indwelling catheter, most commonly in labor with epidural anesthesia in place, the obstetrical catheter is placed in configuration shown in FIG. 1. The catheter tip 20 is inserted into the female urethra and advanced to the insertion marker 70. With the insertion marker 70 at the urethral opening, a syringe with sterile saline is attached to syringe docking port 130 attached to labor balloon check valve 100. A volume of 3 cc of saline is then injected resulting in the inflation of the labor balloon 50. The syringe is then removed from the syringe docking port 130. This allows labor to progress and the fetal vertex to descend without the iatrogenic obstruction related to a large volume catheter while simultaneously keeping the indwelling catheter in place. Should the need arise for a cesarean section, the syringe is then attached to the syringe docking port 130 attached to the standard balloon check valve 110. A volume of 10 cc of saline is then injected resulting in the inflation of the standard balloon 30. The labor balloon 50 is then deflated by removing the 3 cc volume by attaching a empty syringe to the syringe docking port 130 attached to the labor balloon check valve 100 and withdrawing the saline. The labor balloon 50 should not be re-inflated, unless the insertion marker 70 is confirmed to be at the opening of the urethra to avoid inadvertent injury to the urethral structure.

The obstetrical catheter can be used for all other non-labor indications requiring an indwelling catheter because of the retention of the traditional standard balloon 30. This feature allows versatility without requiring the need for additional materials, supplies, or multiple indwelling catheters. It will be apparent that while a preferred embodiment of the invention has been shown and described, various modifications and changes may be made without departing from the true spirit and scope of the invention.

The invention claimed is:

1. A urinary catheter device for obstetrical patients that will allow drainage of urine from a bladder without causing interference or obstruction to a descending fetal head during a labor process, the urinary catheter device comprising:
    a catheter body insertable into a urethra comprising:
        a centrally located urine passage with a central cavity open on both ends to allow the drainage of urine;
        a spherical balloon inflation channel with a central cavity and an inflatable spherical balloon on an indwelling end of the spherical balloon inflation channel and a check valve on an external end of the spherical balloon inflation channel, the check valve preventing inadvertent deflation of the spherical balloon;
        a retaining balloon inflation channel separate from the spherical balloon inflation channel, the retaining balloon inflation channel having a central cavity and a non-spherical flat low-profile-retaining balloon on an indwelling end of the retaining balloon inflation channel, the retaining balloon surrounding a perimeter of the catheter body and being smaller than the spherical balloon, and a check valve on an external end of the retaining balloon inflation channel;
    the spherical balloon positioned closer to an indwelling end of the urine passage than the retaining balloon is;
    wherein the catheter body further comprises an outer layer that incorporates the centrally located urine passage, spherical balloon inflation channel and retaining balloon inflation channel into one single and functional unit.

* * * * *